US005210302A

United States Patent [19]

Sun Pu

[11] Patent Number: 5,210,302

[45] Date of Patent: May 11, 1993

[54] CYCLOBUTENEDIONE DERIVATIVE AND PROCESS FOR PREPARING THE SAME

[75] Inventor: Lyong Sun Pu, Kanagawa, Japan

[73] Assignee: Fuji Xerox Co., Ltd., Tokyo, Japan

[21] Appl. No.: 759,661

[22] Filed: Sep. 13, 1991

[30] Foreign Application Priority Data

Nov. 29, 1990 [JP] Japan .................. 2-333173
Nov. 29, 1990 [JP] Japan .................. 2-333174
Nov. 29, 1990 [JP] Japan .................. 2-333175

[51] Int. Cl.$^5$ .................................. C07C 211/49
[52] U.S. Cl. .................................. 564/307; 257/40
[58] Field of Search ............ 564/307; 357/8, 30, 357/61

[56] References Cited

U.S. PATENT DOCUMENTS 4,986,935 1/1991 Ageishi et al. .................. 252/587

FOREIGN PATENT DOCUMENTS 071117 3/1991 Japan .
112950 5/1991 Japan .
3-112961 5/1991 Japan .

OTHER PUBLICATIONS

Kitipichai et al., Polymer Preprints (Am. Chem. Soc. Div. Polym. Chem.), vol. 32, No. 3, pp. 146-147 (1991).

Primary Examiner—Carolyn Elmore
Assistant Examiner—Scott C. Rand
Attorney, Agent, or Firm—Finnegan, Henderson, Farabow, Garrett and Dunner

[57] ABSTRACT

A novel cyclobutenedione derivative is provided, represented by formula (I):

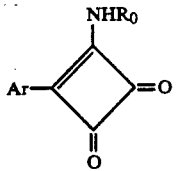

(I)

wherein Ar represents

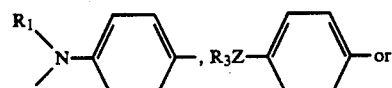

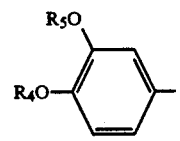

wherein $R_1$ represents a $CH_3$ group or a $C_2H_5$ group; $R_2$ represents a $C_2H_5$ group, a $C_3H_7$ group, a $HOC_2H_4$ group, a $CH_3OC_2H_4$ group or a $CH_3$ group; $R_3$ represents an alkyl group; Z represents O or S; and $R_4$ and $R_5$ each represents an alkyl group, and $R_0$ represents

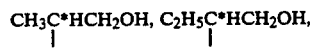

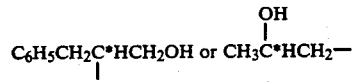

wherein C* represents an asymmetric carbon atom. A process for preparing a cyclobutenedione derivative represented by formula (I) which comprises reacting a cyclobutenedione derivative represented by formula (II) with an amino acid derivative represented by formula (III):

(Abstract continued on next page.)

2 Claims, No Drawings

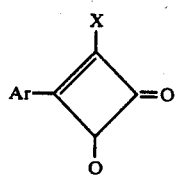
(II)

wherein Ar represents

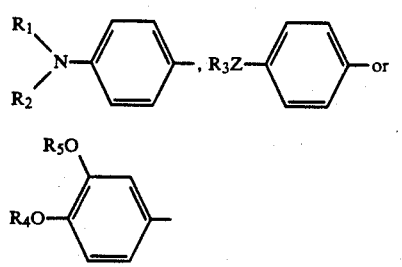

wherein $R_1$ represents a $CH_3$ group or a $C_2H_5$ group, $R_2$ represents a $C_2H_5$ group, a $C_3H_7$ group, a $HOC_2H_4$ group, a $CH_3OC_2H_4$ group or a $CH_3$ group; $R_3$ represents an alkyl group; and $R_4$ and $R_5$ each represents an alkyl group, and X represents a chlorine atom, a bromine atom, a methoxy group or an ethoxy group:

$$NH_2R_0 \qquad (III)$$

wherein $R_0$ represents

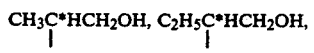

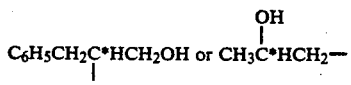

wherein C* represents an asymmetric carbon atom. In a preferred embodiment, the reaction is effected in the presence of a basic compound.

CYCLOBUTENEDIONE DERIVATIVE AND PROCESS FOR PREPARING THE SAME

FIELD OF THE INVENTION

The present invention relates to a novel cyclobutenedione derivative useful as nonlinear optical material and a process for preparing the same.

BACKGROUND OF THE INVENTION

In the field of optical communication and optical data processing, nonlinear optical elements play an important role. A nonlinear optical material to be used for such nonlinear elements is a substance which has extremely important effects on optical signal processing, such as light mixing resulting in the generation of a frequency of sum or difference of two kinds of incident beams having different frequencies, parameteric excitation resulting in the generation of two kinds of lights having different frequencies, Pockels effect or Kerr effect causing the change in the refractive index of light media, conversion of incident beam into secondary harmonics (i.e., SHG) or tertiary harmonics (i.e., THG) and further light bistabilization. As such a nonlinear optical material there has heretofore been mainly used an inorganic material.

As such an inorganic nonlinear optical material, there has been an inorganic crystalline compound such as KDP($KH_2PO_4$) and lithium niobate ($LiNbO_3$). However, such an inorganic crystalline compound leaves is still insufficient.

On the other hand, organic nonlinear optical materials have recently attracted attention as new optical element materials in the field of optoelectronics and thus have been extensively studied more and more every year. In particular, organic compounds having $\pi$ electron conjugated system have been extensively studied for searching of excellent materials in view of excellent properties and high responce of their simple substance.

In general, organic nonlinear optical materials in the crystalline form have a SHG coefficient of 10 to 100 times that of inorganic nonlinear optical materials and a light responce of about 1,000 times that of inorganic nonlinear optical materials. Organic nonlinear optical materials have also been known to exhibit a great shreshold with respect to damage by light.

Examples of organic nonlinear optical materials which have recently been disclosed include organic compounds such as 2-methyl-4-nitroaniline, m-nitroaniline, N-(4-nitrophenyl)-L-prolinol, 2-acetylamino-4-nitro-N,N-dimethylaniline, 4-dimethylamino-4'-nitrostilbene, 4'-dimethylamino-N-methyl-4-stilbazorium-methylsulfate, and 4'-methylbenzylidene-4-nitroaniline. The light nonlinearity of these organic compounds having $\pi$ electron conjugated system is attributed to the interaction between laser beams as electromagnetic wave and $\pi$ electron in the organic compounds. This interaction can be greater by introducing electrophilic and electron donative substituents into the $\pi$ electron conjugated system.

However, such organic compounds generally exhibit a great dipole moment which leads to a great interaction between dipoles upon crystallization, facilitating the formation of a crystal having a structure of symmetry about the center thereof in which the dipole moment of two molecules cancel each other. There is a problem that the secondary nonlinear optical effect, which is important in application, cannot be attained by such a crystal having a symmetry about the center thereof. In order to destroy the symmetry which prevents the attainment of light nonlinearity in crystal state, an approach has been made which comprises introducing substituents having a hydrogen bonding ability or optically active substituents containing asymmetric carbon atoms into an organic compound having $\pi$ electron conjugated system upon design of molecules. The inventors proposed a material comprising optically active substituents containing asymmetric carbon atoms incorporated in $\pi$ electron conjugated system in JP-A-3-112961 (the term "JP-A" as used herein means an "unexamined published Japanese patent application"). However, none of these proposed materials attain sufficient optical nonlinearity, storage stability and workability.

In general, materials for nonlinear optical element are required to exhibit enough light non-linearity, light transmission, laser resistance, crystallizability, phase adjustability, workability, mechanical strength, hygroscopicity, hardness, etc.

It has been extremely difficult to select among organic nonlinear optical element materials which have heretofore been known those satisfying the above mentioned practically necessary requirements.

SUMMARY OF THE INVENTION

An object of the present invention is to provide a practical organic nonlinear optical element material which provides improvements in these requirements, e.g., nonlinear optical effect, storage stability, workability and transparency.

The above object of the present invention will beccome more apparent from the following detailed description and examples.

The inventors found that even a compound system having a great molecular dipole moment which can form a symmetry about the center thereof upon crystallization can provide an organic nonlinear optical element material having a great secondary nonlinear optical effect in particular by introducing proper substituents into the molecule.

The above object of the present invention is accomplished with a cyclobutenedione derivative, represented by formula (I):

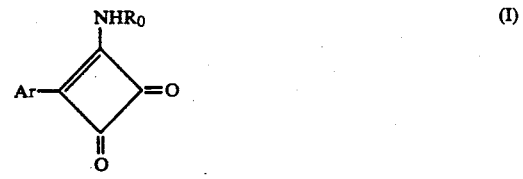

wherein Ar represents

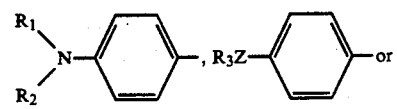

-continued

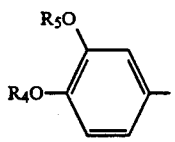

wherein $R_1$ represents a $CH_3$ group or a $C_2H_5$ group, $R_2$ represents a $C_2H_5$ group, a $C_3H_7$ group, a $HOC_2H_4$ group, a $CH_3OC_2H_4$ group or a $CH_3$ group; $R_3$ represents an alkyl group; Z represents O or S; and $R_4$ and $R_5$ each represents an alkyl group, and $R_0$ represents

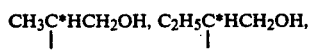

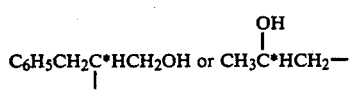

wherein C* represents an asymmetric carbon atom, and further a process for preparing a cyclobutenedione derivative which comprises reacting a cyclobutenedione derivative represented by formula (II) with an amino acid derivative represented by formula (III):

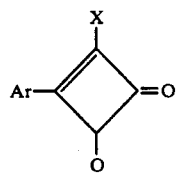 (II)

wherein Ar represents

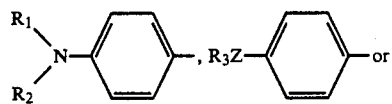

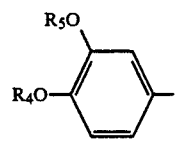

wherein $R_1$ represents a $CH_3$ group or a $C_2H_5$ group; $R_2$ represents a $C_2H_5$ group, a $C_3H_7$ group, a $HOC_2H_4$ group, a $CH_3OC_2H_4$ group or a $CH_3$ group; $R_3$ represents an alkyl group; and $R_4$ and $R_5$ each represents an alkyl group; and X represents a chlorine atom, a bromine atom, a methoxy group or an ethoxy group:

$NH_2R_0$ (III)

wherein $R_0$ represents

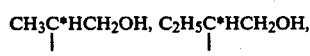

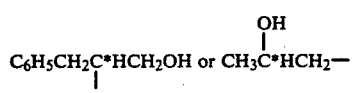

wherein C* represents an asymmetric carbon atom.

DETAILED DESCRIPTION OF THE INVENTION

The cyclobutenedione ring contained in the cyclobutenedione derivative of the present invention represented by formula (I) exhibits as strong electrophilicity as a nitro group as can be seen from the maximum absorption wavelength (intramolecular charge-transfer absorption band). The cyclobutenedione ring also has a long $\pi$ electron conjugated system. Therefore, it can easily be in a structure in which the molecule generally shows an electrically big polarization, causing the occurrence of a high nonlinearity.

In the cyclobutenedione derivative represented by formula (I) comprising a substituent having asymmetric carbon atoms incorporated therein, even if the dipole moment of the molecule itself is great, a greater light nonlinearity can be attained by controlling the molecular orientation in bulk structure so that the symmetry about the center thereof is destroyed.

The cyclobutenedione derivative of the present invention represented by formula (I) can be readily synthesized in a high yield by the following reaction formula:

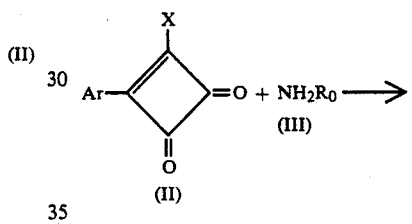

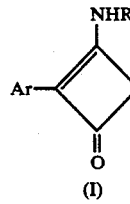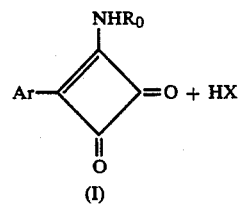

wherein Ar represents

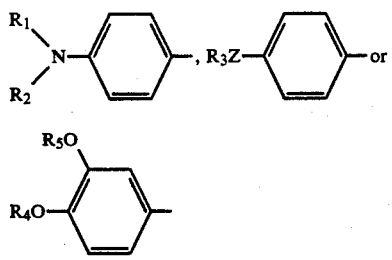

wherein $R_1$ represents a $CH_3$ group or a $C_2H_5$ group; $R_2$ represents a $C_2H_5$ group, a $C_3H_7$ group, a $HOC_2H_4$ group, a $CH_3OC_2H_4$ group or a $CH_3$ group; $R_3$ represents an alkyl group (preferably having 1 to 20 carbon atoms and particularly preferably 1 to 6 carbon atoms); and $R_4$ and $R_5$ each represents an alkyl group (preferably having 1 to 20 carbon atoms and particularly preferably 1 to 6 carbon atoms); Z represents O or S; and X represents a chlorine atom, a bromine atom, a methoxy group or an ethoxy group:

NH$_2$R$_0$ (III)

wherein R$_0$ represents

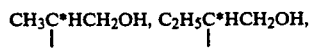

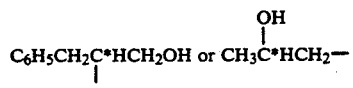

wherein C* represents an asymmetric carbon atom.

In particular, a cyclobutenedion derivative represented by formula (II) is suspended or dissolved in a solvent such as acetone, tetrahydrofuran, methanol and ethanol. An amino acid derivative represented by formula (III) is then gradually added to the suspension or solution thus obtained in an amount equivalent to the cyclobutenedione derivative or more with stirring to effect reaction. The reaction normally proceeds quickly. However, the reaction may be optionally effected under heating (i.e., reflux temperature). If as the reaction proceeds, the product deposits, it is then filtered. If the product doesn't deposit, the reaction system is concentrated or a proper poor solvent is added to the reaction system to allow the product to deposit. The resulting crystal is optionally recrystallized from a solvent such as alcohol and acetone or sublimed so that it is purified.

Instead of using an amino acid derivative represented by formula (III), its acid addition product (salt) such as hydrochloride, bromate and p-toluenesulfonate may be used as starting material. The starting material may be reacted with a cyclobutenedione derivative represented by formula (II) in the presence of a basic compound such as triethylamine and N-methylmorpholine in the same manner as mentioned above.

The preparation of a cyclobutenedione derivative represented by formula (II) can be accomplished by a process which comprises mixing an aromatic compound represented by formula, Ar-H and dichlorocyclobutenedione in a Friedel-Crafts solvent such as carbon disulfide, nitrobenzene and methylene chloride optionally in the presence of aluminum chloride with stirring to obtain a chlorocyclobutenedione derivative or a process which comprises reacting dialkoxycyclobutenedione with an aromatic compound represented by formula, Ar-H with a trialkyloxonium salt or a halogenating solvent to obtain an alkoxycyclobutenedione derivative.

The present invention will be further described in the following examples, but the present invention should not be construed as being limited thereto.

EXAMPLE I-1

Synthesis of 1-(4'-N,N-diethylaminophenyl)-2-(1'-hydroxymethylethylamino)-cyclobutene-3,4-dione 2 g of S-(+)-2-amino-1-propanol was added to 100 ml of an acetone solution containing 2 g (7.6 mmol) of a compound represented by structural formula (II-1). The obtained mixture was then stirred for about 2 hours.

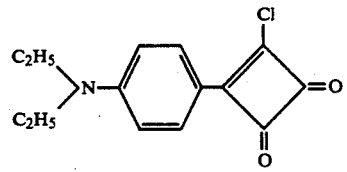

After the completion of the reaction, the material was then evaporated to dryness. The resulting residue was recrystallized from methanol to obtain 0.8 g (2.7 mmol) of 1-(4'-N,N-diethylaminophenyl)-2-(1'-hydroxymethylethylamino)-cyclobutene-3,4-dione represented by structural formula (I-1) in the form of yellow crystal.

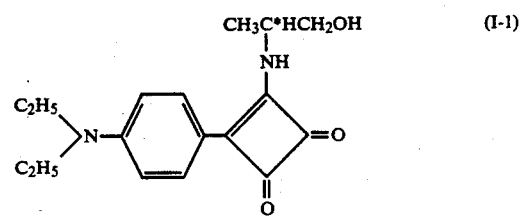

The yield was 36%. The product exhibited the following properties:
Melting point: 166° C.
Maximum absorption wavelength (λmax): 407 nm (in CH$_2$Cl$_2$)

| | Elementary analysis: | | |
|---|---|---|---|
| | C | H | N |
| Calculated % | 67.52 | 7.34 | 9.27 |
| Found % | 67.71 | 7.31 | 9.15 |

EXAMPLES I-2–I-12

Target products described in the column of formula (I) in Tables I-1 to I-4 were synthesized in the same manner as in Example I-1 except that as starting materials there were used cyclobutenedione derivatives described in the column of formula (II) in Tables I-1 to I-4 and amino acid derivatives described in the column of formula (III) in Tables I-1 to I-4. The resulting products were then measured for maximum absorption wavelength (λmax in CH$_2$Cl$_2$) and melting point and subjected to elementary analysis. The results are shown in Table I-5.

A glass cell packed with the compound represented by structural formula (I-1) described in Example I-1 in the form of powder was irradiated with Nd:YAG laser (wavelength: 1.064 μm; output: 180 mJ/pulse). As a result, a strong green scattered light having a wavelength of 532 nm due to SHG was emitted efficiently.

The cyclobutenedione derivatives of the present invention represented by the above mentioned formulae are novel compounds which exhibit a high nonlinearity and excellent heat resistance, light resistance, storage stability and workability and thus can be used to prepare a nonlinear optical element such as light wavelength conversion element, light shutter, fast light switching element, light logical gate and phototransistor.

TABLE I-1

| Example No. | Formula (II) (cyclobutenedione derivative) | Formula (III) (Amino acid derivative) | Formula (I) (Target product) |
|---|---|---|---|
| Example I-2 | [4-(diethylamino)phenyl chlorocyclobutenedione structure with $C_2H_5$ groups on N] | $NH_2CH_2\overset{OH}{\underset{}{C^*HCH_3}}$ | [product with $NHCH_2C^*HCH_3$ substituent and OH] |
| Example I-3 | [same cyclobutenedione as I-2] | $C_2H_5C^*HCH_2OH$<br>$NH_2$ | [product with $C_2H_5C^*HCH_2OH$ / NH substituent] |
| Example I-4 | [same cyclobutenedione as I-2] | $C_6H_5CH_2C^*HCH_2OH$<br>$NH_2$ | [product with $C_6H_5CH_2C^*HCH_2OH$ / NH substituent] |

TABLE I-2

| Example No. | Formula (II) (cyclobutenedione derivative) | Formula (III) (Amino acid derivative) | Formula (I) (Target product) |
|---|---|---|---|
| Example I-5 | [4-(N-methyl-N-ethylamino)phenyl chlorocyclobutenedione] | $NH_2CH_2\overset{OH}{\underset{}{C^*HCH_3}}$ | [product with $NHCH_2C^*HCH_3$ / OH substituent] |
| Example I-6 | [same cyclobutenedione as I-5] | $CH_3C^*HCH_2OH$<br>$NH_2$ | [product with $CH_3C^*HCH_2OH$ / NH substituent] |
| Example I-7 | [same cyclobutenedione as I-5] | $C_2H_5C^*HCH_2OH$<br>$NH_2$ | [product with $C_2H_5C^*HCH_2OH$ / NH substituent] |

TABLE I-3

| Example No. | Formula (II) (cyclobutenedione derivative) | Formula (III) (Amino acid derivative) | Formula (I) (Target product) |
|---|---|---|---|
| Example I-8 | [structure: 4-(N-methyl-N-ethylamino)phenyl cyclobutenedione with Cl] | $C_6H_5CH_2C^*HCH_2OH$ / $NH_2$ | [structure: product with $C_6H_5CH_2C^*HCH_2OH$ / NH group] |
| Example I-9 | [structure: 4-(N-methyl-N-hydroxyethyl)aminophenyl cyclobutenedione with Cl] | $CH_3C^*HCH_2OH$ / $NH_2$ | [structure: product with $CH_3C^*HCH_2OH$ / NH group] |
| Example I-10 | [structure: 4-(N-methyl-N-hydroxyethyl)aminophenyl cyclobutenedione with Cl] | $NH_2CH_2C^*HCH_3$ / OH | [structure: product with OH / $NHCH_2C^*HCH_3$ group] |

TABLE I-4

| Example No. | Formula (II) (cyclobutenedione derivative) | Formula (III) (Amino acid derivative) | Formula (I) (Target product) |
|---|---|---|---|
| Example I-11 | [structure: 4-(N-methyl-N-methoxyethyl)aminophenyl cyclobutenedione with Cl] | $NH_2CH_2C^*HCH_3$ / OH | [structure: product with OH / $NHCH_2C^*HCH_3$] |
| Example I-12 | [structure: 4-(N-methyl-N-methoxyethyl)aminophenyl cyclobutenedione with Cl] | $C_2H_5C^*HCH_2OH$ / $NH_2$ | [structure: product with $C_2H_5C^*HCH_2OH$ / NH] |

TABLE I-5

| Example No. | Elementary analysis (calculated %/found %) | | | λmax (nm) | M.P. (°C.) |
|---|---|---|---|---|---|
| | C | H | N | | |
| Example I-2 | 67.52/67.73 | 7.34/7.31 | 9.27/9.15 | 406 | 227 |
| Example I-3 | 68.33/68.13 | 7.65/7.62 | 8.86/8.91 | 407 | 165 |
| Example I-4 | 72.99/72.85 | 6.93/6.90 | 7.40/7.53 | 407 | 152 |
| Example I-5 | 66.64/66.73 | 6.99/6.88 | 9.72/9.65 | 404 | 229 |
| Example I-6 | 66.64/66.45 | 6.99/6.75 | 9.72/9.55 | 404 | 193 |
| Example I-7 | 67.52/67.73 | 7.34/7.12 | 9.27/9.05 | 404 | 147 |
| Example I-8 | 72.50/72.21 | 6.64/6.63 | 7.69/7.73 | 404 | 166 |
| Example I-9 | 64.13/64.51 | 6.97/6.86 | 8.80/8.74 | 403 | 155 |
| Example I-10 | 64.13/64.46 | 6.97/6.85 | 8.80/8.62 | 402 | 206 |
| Example I-11 | 64.13/64.35 | 6.97/6.95 | 8.80/8.72 | 401 | 196 |
| Example I-12 | 65.04/65.32 | 7.28/7.15 | 8.43/8.35 | 401 | 138 |

EXAMPLE II-1

Synthesis of 1-(4'-methylthiophenyl)-2-(1'-hydroxymethyl-2'-phenylethylamino)-cyclobutene-3,4-dione 1 g of D-phenylalaninol was added to 30 ml of an acetone solution containing 1 g (4.2 mmol) of a compound represented by structural formula (II-2):

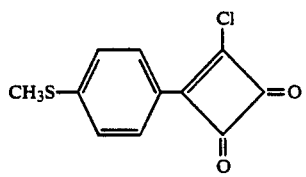

(II-2)

The obtained mixture was then stirred for about 2 hours. After the completion of the reaction, 20 ml of water was added to the system as poor solvent. The material was then allowed to stand in a refrigerator. The resulting yellow crystal was recovered to obtain 1.2 g (3.4 mmol) of 1-(4'-methylthiophenyl)-2-(1'-hydroxymethyl-2'-phenylethylamino)-cyclobutene-3,4-dione in the form of yellow crystal. The yield was 81%.

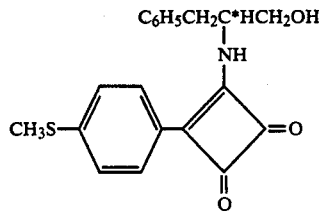

(I-2)

The product exhibited the following properties:
Melting point: 191° C.
Maximum absorption wavelength (λmax): 366 nm (in $CH_2Cl_2$)

| | Elementary analysis: | | |
|---|---|---|---|
| | C | H | N |
| Calculated % | 67.96 | 5.42 | 3.96 |
| Found % | 67.85 | 5.40 | 3.88 |

EXAMPLES II-2–II-9

Target products described in the column of formula (I) in Tables II-1 to II-3 were synthesized in the same manner as in Example II-1 except that as starting materials there were used cyclobutenedione derivatives described in the column of formula (II) in Tables II-1 to II-3 and amino acid derivatives described in the column of formula (III) in Tables II-1 to II-3.

The resulting products were then measured for maximum absorption wavelength (λmax in $CH_2Cl_2$) and melting point and subjected to elementary analysis. The results are shown in Table II-4.

A glass cell packed with the compound represented by structural formula (I-2) described in Example II-1 in the form of powder was irradiated with Nd:YAG laser (wavelength: 1.064 μm; output: 180 mJ/pulse). As a result, a strong green scattered light having a wavelength of 532 nm due to SHG was emitted efficiently.

The cyclobutenedione derivatives of the present invention represented by the above mentioned formulae are novel compound which exhibit a high nonlinearity and excellent heat resistance, light resistance, storage stability and workability and thus can be used to prepare a nonlinear optical element such as light wavelength conversion element, light shutter, fast light switching element, light optical gate and phototransistor.

TABLE II-1

| Example No. | Formula (II) (cyclobutenedione derivative) | Formula (III) (Amino acid derivative) | Formula (I) (Target product) |
|---|---|---|---|
| Example II-2 | [structure: $CH_3O$—C6H4—cyclobutenedione with Cl] | $CH_3C^*HCH_2OH$ / $NH_2$ | [structure: $CH_3O$—C6H4—cyclobutenedione with NH—$C^*HCH_3$—$CH_2OH$] |
| Example II-3 | [structure: $CH_3O$—C6H4—cyclobutenedione with Cl] | OH / $NH_2CH_2C^*HCH_3$ | [structure: $CH_3O$—C6H4—cyclobutenedione with NHCH$_2$C*HCH$_3$—OH] |
| Example II-4 | [structure: $CH_3O$—C6H4—cyclobutenedione with Cl] | $C_2H_5C^*HCH_2OH$ / $NH_2$ | [structure: $CH_3O$—C6H4—cyclobutenedione with NH—$C_2H_5C^*HCH_2OH$] |

TABLE II-2

| Example No. | Formula (II) (cyclobutenedione derivative) | Formula (III) (Amino acid derivative) | Formula (I) (Target product) |
|---|---|---|---|
| Example II-5 | 3-(4-methoxyphenyl)-4-chlorocyclobutene-1,2-dione | $C_6H_5CH_2C^*HCH_2OH$<br>$\quad\mid$<br>$\quad NH_2$ | corresponding 3-amino substituted product |
| Example II-6 | 3-(4-methylthiophenyl)-4-chlorocyclobutene-1,2-dione | $\quad\;\;OH$<br>$\quad\;\;\mid$<br>$NH_2CH_2C^*HCH_3$ | corresponding 3-amino substituted product |
| Example II-7 | 3-(4-methylthiophenyl)-4-chlorocyclobutene-1,2-dione | $C_2H_5C^*HCH_2OH$<br>$\quad\mid$<br>$\quad NH_2$ | corresponding 3-amino substituted product |

TABLE II-3

| Example No. | Formula (II) (cyclobutenedione derivative) | Formula (III) (Amino acid derivative) | Formula (I) (Target product) |
|---|---|---|---|
| Example II-8 | 3-(4-methylthiophenyl)-4-chlorocyclobutene-1,2-dione | $CH_3C^*HCH_2OH$<br>$\quad\mid$<br>$\quad NH_2$ | corresponding 3-amino substituted product |
| Example II-9 | 3-(4-methylthiophenyl)-4-chlorocyclobutene-1,2-dione | $\quad\;\;OH$<br>$\quad\;\;\mid$<br>$NH_2CH_2C^*HC_2H_5$ | corresponding 3-amino substituted product |

TABLE II-4

| Example No. | Elementary analysis (calculated %/found %) | | | λmax (nm) | M.P. (°C.) |
|---|---|---|---|---|---|
| | C | H | N | | |
| Example II-2 | 64.35/64.26 | 5.79/5.75 | 5.36/5.42 | 351 | 205 |
| Example II-3 | 64.35/64.52 | 5.79/5.76 | 5.36/5.40 | 351 | 217 |
| Example II-4 | 65.44/65.56 | 6.23/6.15 | 5.09/5.12 | 351 | 155 |
| Example II-5 | 71.20/71.42 | 5.68/5.65 | 4.15/4.32 | 351 | 187 |
| Example II-6 | 60.63/60.51 | 5.45/5.40 | 5.05/5.13 | 366 | 216 |
| Example II-7 | 65.44/65.64 | 6.23/6.20 | 5.09/5.15 | 366 | 160 |
| Example II-8 | 60.63/60.41 | 5.45/5.56 | 5.50/5.45 | 366 | 202 |
| Example II-9 | 61.83/61.62 | 5.88/5.85 | 4.81/4.90 | 366 | 206 |

EXAMPLE III-1

Synthesis of 1-(3',4'-dimethoxyphenyl)-2-(1'-hydroxymethyl-2'-phenylethylamino)-cyclobutene-3,4-dione 1 g of D-phenylalaninol was added to 20 ml of an acetone solution containing 0.6 g (2.4 mmol) of a compound represented by structural formula (II-3):

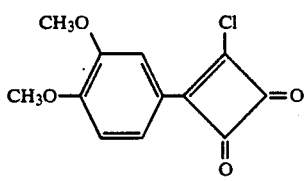

(II-3)

The obtained mixture was then stirred for about 2 hours. After the completion of the reaction, 40 ml of water was added to the system as poor solvent. The material was then allowed to stand in a refrigerator. The resulting yellow crystal was recovered to obtain 0.5 g (1.4 mmol) of 1-(3',4'-dimethoxyphenyl)-2-(1'-hydroxymethyl-2'-phenylethylamino)-cyclobutene-3,4-dione in the form of yellow crystal. The yield was 58%.

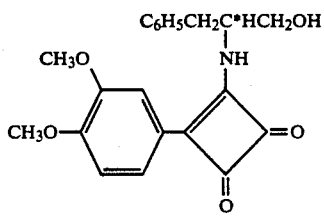

(I-3)

The product exhibited the following properties:
Melting point: 192° C.
Maximum absorption wavelength (λmax): 358 nm (in $CH_2Cl_2$)

| | Elementary analysis: | | |
|---|---|---|---|
| | C | H | N |
| Calculated % | 68.65 | 5.76 | 3.81 |
| Found % | 68.46 | 5.40 | 3.92 |

EXAMPLES III-2–III-4

Target products described in the column of formula (I) in Table III-1 were synthesized in the same manner as in Example III-1 except that as starting materials there were used cyclobutenedione derivatives described in the column of formula (II) in Table III-1 and amino acid derivatives described in the column of formula (III) in Table III-1.

The resulting products were then measured for maximum absorption wavelength (λmax in $CH_2Cl_2$) and melting point and subjected to elementary analysis. The results are shown in Table III-2.

A glass cell packed with the compound represented by structural formula (I-3) described in Example III-1 in the form of powder was irradiated with Nd:YAG laser (wavelength: 1.064 μm; output: 180 mJ/pulse). As a result, a strong green scattered light having a wavelength of 532 nm due to SHG was emitted efficiently.

The cyclobutenedione derivatives of the present invention represented by the above mentioned formulae are novel compound which exhibit a high nonlinearity and excellent heat resistance, light resistance, storage stability and workability and thus can be used to prepared a nonlinear optical element such as light wavelength conversion element, light shetter, fast light switching element, light logical gate and phototransistor.

TABLE III-1

| Example No. | Formula (II) (cyclobutenedione derivative) | Formula (III) (Amino acid derivative) | Formula (I) (Target product) |
|---|---|---|---|
| Example III-2 | [CH3O, CH3O-phenyl-cyclobutenedione with Cl] | CH3C*HCH2OH, NH2 | [CH3O, CH3O-phenyl-cyclobutenedione with NH-C*HCH2OH-CH3] |
| Example III-3 | [CH3O, CH3O-phenyl-cyclobutenedione with Cl] | OH, NH2CH2C*HCH3 | [CH3O, CH3O-phenyl-cyclobutenedione with NHCH2C*HCH3-OH] |
| Example III-4 | [CH3O, CH3O-phenyl-cyclobutenedione with Cl] | C2H5C*HCH2OH, NH2 | [CH3O, CH3O-phenyl-cyclobutenedione with NH-C*HCH2OH-C2H5] |

TABLE III-2

| Example No. | Elementary analysis (calculated %/found %) | | | λmax (nm) | M.P. (°C.) |
| --- | --- | --- | --- | --- | --- |
| | C | H | N | | |
| Example III-2 | 62.06/62.25 | 5.56/5.32 | 4.83/4.78 | 359 | 213 |
| Example III-3 | 61.84/61.58 | 5.83/5.62 | 4.81/4.85 | 358 | 185 |
| Example III-4 | 62.94/62.85 | 6.27/6.35 | 4.59/4.62 | 358 | 163 |

While the invention has been described in detail and with reference to specific embodiments thereof, it will be apparent to one skilled in the art that various changes and modifications can be made therein without departing from the spirit and scope thereof.

What is claimed is:

1. A cyclobutenedione derivative, represented by formula (I):

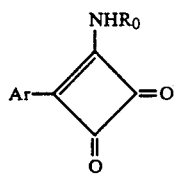

(I)

wherein Ar represents

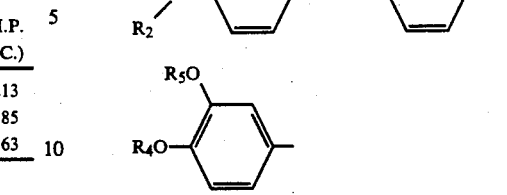

wherein $R_1$ represents a $CH_3$ group or a $C_2H_5$ group; $R_2$ represents a $C_2H_5$ group, a $C_3H_7$ group, a $HOC_2H_4$ group, a $CH_3OC_2H_4$ group or a $CH_3$ group; $R_3$ represents an alkyl group; Z represents O or S; and $R_4$ and $R_5$ each represents an alkyl group, and $R_0$ represents

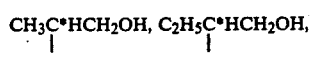

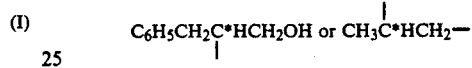

wherein C* represents an asymmetric carbon atom.

2. A cyclobutenedione derivative as in claim 1, wherein $R_3$, $R_4$ and $R_5$ each represents an alkyl group having 1 to 6 carbon atoms.